United States Patent
Kojima

(10) Patent No.: US 10,517,548 B2
(45) Date of Patent: Dec. 31, 2019

(54) X-RAY DIAGNOSTIC APPARATUS AND CONTROL METHOD FOR X-RAY DIAGNOSTIC APPARATUS

(71) Applicant: TOSHIBA MEDICAL SYSTEMS CORPORATION, Otawara-Shi (JP)

(72) Inventor: Tsuyoshi Kojima, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 894 days.

(21) Appl. No.: 14/824,111

(22) Filed: Aug. 12, 2015

(65) Prior Publication Data

US 2015/0342557 A1    Dec. 3, 2015

Related U.S. Application Data

(63) Continuation of application No. PCT/JP2014/053064, filed on Feb. 10, 2014.

(30) Foreign Application Priority Data

Feb. 12, 2013    (JP) .................................. 2013-024897

(51) Int. Cl.
     *A61B 6/00*      (2006.01)
     *A61B 6/10*      (2006.01)
     *A61B 6/04*      (2006.01)

(52) U.S. Cl.
     CPC ............ *A61B 6/102* (2013.01); *A61B 6/4441* (2013.01); *A61B 6/547* (2013.01); *A61B 6/0457* (2013.01)

(58) Field of Classification Search
None
See application file for complete search history.

(56) References Cited

U.S. PATENT DOCUMENTS

| | | | | |
|---|---|---|---|---|
| 7,746,978 B2 * | 6/2010 | Cheng | .................... | A61N 5/107 378/197 |
| 8,126,224 B2 * | 2/2012 | Zuhars | ..................... | A61B 6/12 378/197 |

(Continued)

FOREIGN PATENT DOCUMENTS

| | | |
|---|---|---|
| JP | 2001-276030 A | 10/2001 |
| JP | 2002-238888 A | 8/2002 |

(Continued)

OTHER PUBLICATIONS

Office Action dated Feb. 14, 2017 in Japanese Patent Application No. 2013-024897.

(Continued)

*Primary Examiner* — Hoon K Song
(74) *Attorney, Agent, or Firm* — Oblon, McClelland, Maier & Neustadt, L.L.P.

(57) ABSTRACT

There is provided an X-ray diagnostic apparatus which comprises a top, a bed, an X-ray tube, an X-ray detector, a supporting arm configured to movably support the X-ray tube generation unit and the X-ray detector, a holder configured to movably hold the supporting arm and control processing circuitry. The control processing circuitry controls the bed, the supporting arm, and the holder to limit movement of the top, the X-ray tube, the X-ray detector, and the supporting arm based on distances between the top, the X-ray tube, the X-ray detector, and the supporting arm, and moving directions of the top, the X-ray tube, the X-ray detector, and the supporting arm.

19 Claims, 10 Drawing Sheets

(56) References Cited

U.S. PATENT DOCUMENTS

| | | | |
|---|---|---|---|
| 2006/0285644 A1 | 12/2006 | Camus | |
| 2007/0200396 A1* | 8/2007 | Baumann | A61B 6/0457 297/135 |
| 2008/0056451 A1* | 3/2008 | Gotoh | A61B 6/4441 378/197 |
| 2008/0258929 A1 | 10/2008 | Maschke | |
| 2009/0022275 A1* | 1/2009 | Grebner | A61B 6/102 378/95 |
| 2014/0334602 A1* | 11/2014 | Narabu | A61B 6/0407 378/62 |

FOREIGN PATENT DOCUMENTS

| | | |
|---|---|---|
| JP | 2006-026286 A | 2/2006 |
| JP | 2007-215584 A | 8/2007 |
| JP | 2007-268060 A | 10/2007 |
| JP | 2008-148866 A | 7/2008 |
| JP | 2008-272290 A | 11/2008 |
| JP | 2009-022602 A | 2/2009 |

OTHER PUBLICATIONS

International Search Report dated Mar. 11, 2014 in PCT/JP2014/053064 filed Feb. 10, 2014 (with English translation).
Written Opinion dated Mar. 11, 2014 in PCT/JP2014/053064 filed Feb. 10, 2014.

* cited by examiner

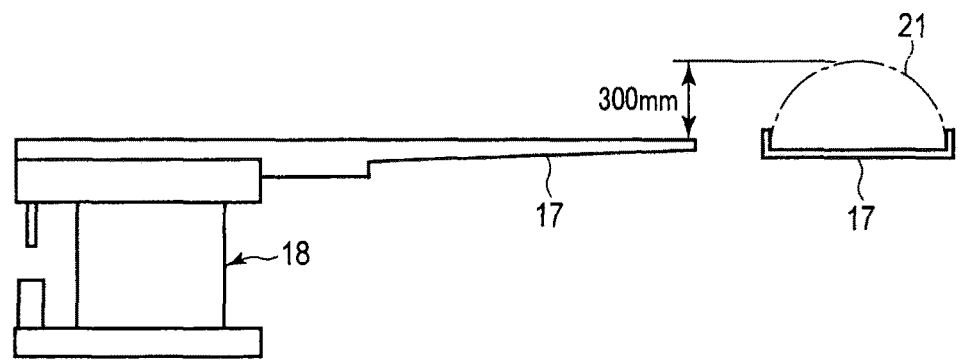
F I G. 9
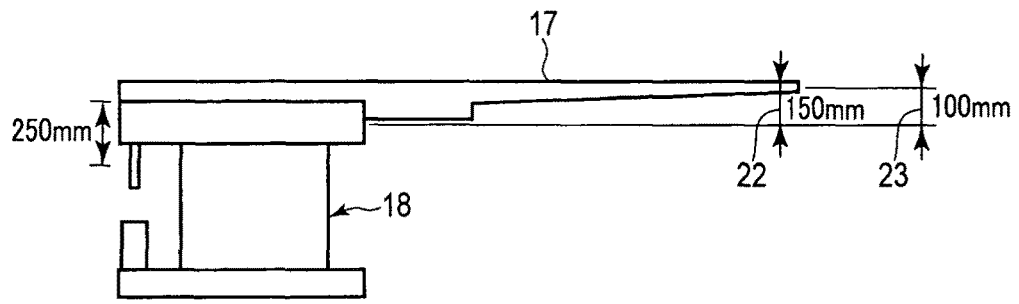
F I G. 10
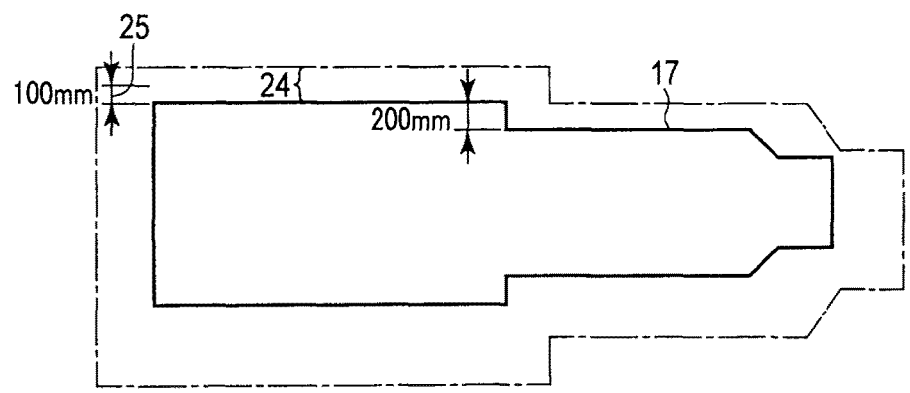
F I G. 11

X-RAY DIAGNOSTIC APPARATUS AND CONTROL METHOD FOR X-RAY DIAGNOSTIC APPARATUS

CROSS-REFERENCE TO RELATED APPLICATIONS

This application is a Continuation application of PCT Application No. PCT/JP2014/053064, filed Feb. 10, 2014 and based upon and claims the benefit of priority from the Japanese Patent Application No. 2013-024897, filed Feb. 12, 2013, the entire contents of all of which are incorporated herein by reference.

FIELD

Embodiments described herein relate generally to an X-ray diagnostic apparatus having an arm such as a C-arm, and a control method for the X-ray diagnostic apparatus.

BACKGROUND

A medical image diagnostic technique using an X-ray diagnostic apparatus, an MRI apparatus, an X-ray CT apparatus, or the like has rapidly progressed with advances in computer technology, and become indispensable to today's medical care.

Recently, X-ray diagnosis has advanced mainly in the field of circulatory organs with improvements in catheter techniques. For example, in general, an X-ray image diagnostic apparatus for diagnosis of circulatory organs moves an imaging unit including an X-ray generation unit, an X-ray detector, and a C-arm which supports them, thereby allowing imaging of an object placed on a top from an optimum angle. Furthermore, the X-ray image diagnostic apparatus moves the X-ray detector close to an imaging portion of the object, thereby allowing imaging from an optimum position.

Since the imaging unit is moved near the object, it may be brought into contact with the object. To avoid this problem, there is known a method of avoiding damage or injury due to contact or the like by stopping the movement of the moving portion when the imaging unit is brought into contact with the top, a patient, or the like, by detecting the speed of the moving portion, the current and/or power to a driving means, the position of the moving portion, and the like.

In a technique disclosed in patent literature 1, for example, the external dimensions of an object placed on a top are calculated using three-dimensional image data of the object acquired by X-ray fluoroscopy from a plurality of angles, and an interference avoidance region corresponding to the outline of the object is set based on the calculated dimensions. When an imaging unit enters the set interference avoidance region, the moving speed of the imaging unit is decelerated.

In conventional interference control described above, interference points are set in portions (portions of interest) of the X-ray diagnostic apparatus, with which interference (contact) readily occurs, the three-dimensional positions (XYZ coordinates) of the interference points are calculated in consideration of the positions (angles and distances) of respective movable axes, and the clearance between each interference point and an interference (contact) target object (for example, a still object or moving object) is calculated. Before interference (contact) actually occurs, a warning sound is generated and a warning is displayed to indicate that interference will occur, and a corresponding axial operation is decelerated/stopped.

In conventional interference control, processing of calculating the coordinates of each interference point and processing of calculating the distance between the interference point and a target object are performed for each processing loop of the firmware of the X-ray diagnostic apparatus. Therefore, the clearance between the target object and each interference point at given time is compared with a predetermined threshold to perform determination, and the interference operation is controlled based on the result. The space coordinates of each interference point are generated and updated based on the latest position information and angle information of each movable axis during control processing every time the processing loop is executed.

In such conventional interference control, since control is not executed in consideration of the moving direction (operating direction of each movable axis) and moving speed (operating speed of each movable axis) of each interference point, it is impossible to detect the acceleration when the plurality of movable axes simultaneously operate or noninterference (the axes pass each other but are not brought into contact with each other) when the movable axes operate parallelly. Therefore, in conventional interference control, it is difficult to suppress the more precise interference operation in consideration of the operating speed and operating direction of each movable axis.

BRIEF DESCRIPTION OF THE DRAWINGS

FIG. 9 is a view showing a deceleration region for the patient barrier of the X-ray diagnostic apparatus according to the embodiment of the present invention.

FIG. 10 is a view showing a deceleration region and warning region with respect to the bottom surface of the bed/top of the X-ray diagnostic apparatus according to the embodiment of the present invention.

FIG. 11 is a view showing a deceleration region and warning region around the bed/top of the X-ray diagnostic apparatus according to the embodiment of the present invention.

DETAILED DESCRIPTION

According to one embodiment, there is provided an X-ray diagnostic apparatus which comprises a top, a bed, an X-ray tube, an X-ray detector, a supporting arm configured to movably support the X-ray tube generation unit and the X-ray detector, a holder configured to movably hold the supporting arm and control processing circuitry. The control processing circuitry controls the bed, the supporting arm, and the holder to limit movement of the top, the X-ray tube, the X-ray detector, and the supporting arm based on distances between the top, the X-ray tube, the X-ray detector, and the supporting arm, and moving directions of the top, the X-ray tube, the X-ray detector, and the supporting arm.

An X-ray diagnostic apparatus and a control method for the X-ray diagnostic apparatus according to an embodiment of the present invention will be described below with reference to the accompanying drawings.

Figure 1:
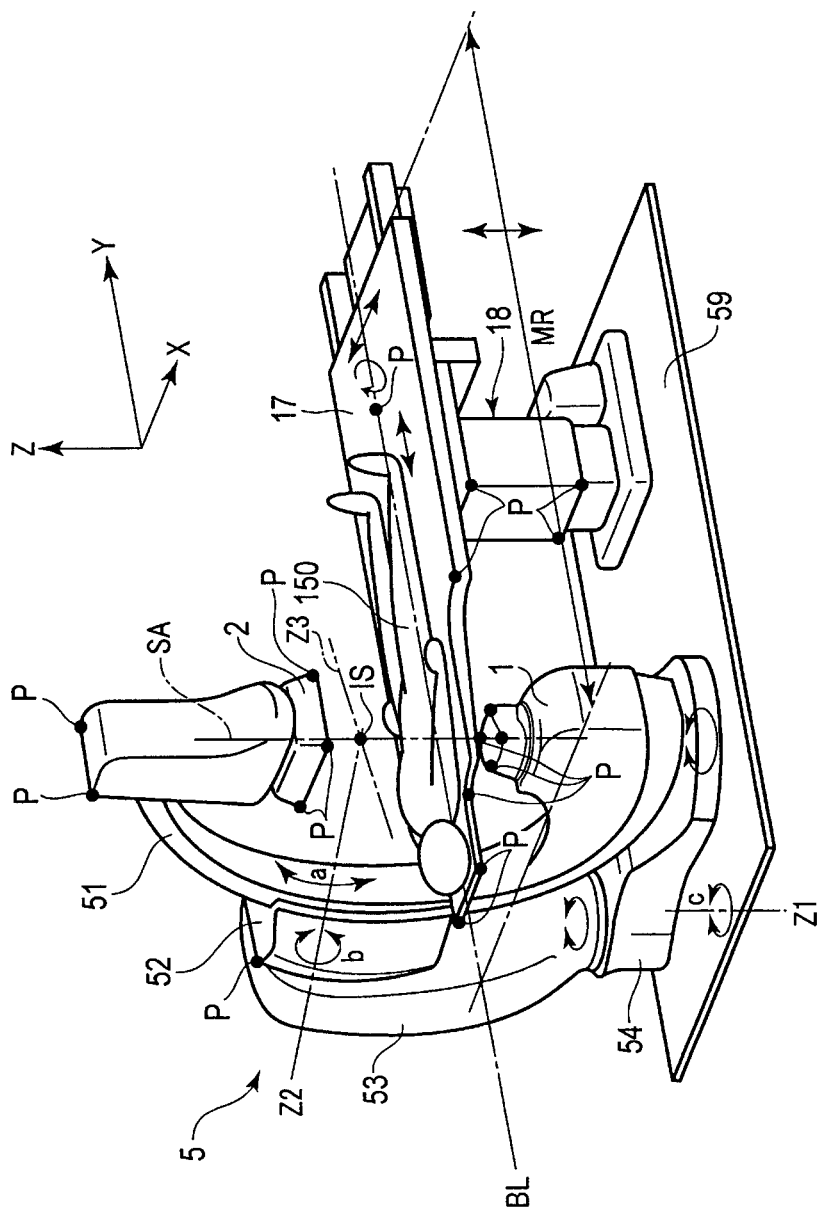
FIG. 1 is a view showing the outer appearance of an X-ray diagnostic apparatus according to an embodiment of the present invention.

FIG. 1 is a view showing the outer appearance of the X-ray diagnostic apparatus according to the embodiment of the present invention.

As shown in FIG. 1, a stand 53 is supported on one end of a floor swing arm 54 so as to be rotatable (in directions indicated by a double-headed arrow c) about a column rotation axis Z1 almost perpendicular to a floor surface 59.

An arm holder 52 is supported on the stand 53 so as to be rotatable (in directions indicated by a double-headed arrow b) about a main arm rotation axis Z2 almost parallel to the floor surface 59.

A C-arm 51 is supported on the arm holder 52 so as to be slidably rotatable (in directions indicated by a double-headed arrow a) about an arm slide axis Z3 which is perpendicular to the main arm rotation axis Z2 and almost parallel to the floor surface 59.

As described above, a holding apparatus main body 5 including the floor swing arm 54, stand 53, and arm holder 52 holds the C-arm 51 so as to be rotatable about the column rotation axis Z1, main arm rotation axis Z2, and arm slide axis Z3.

The column rotation axis Z1, main arm rotation axis Z2, and arm slide axis Z3 are operation axes which dominantly determine the values of "clinical angles (LAO/RAO or CRA/CAU) as clinical angular directions" serving as important elements to position a diagnosis target portion of an object 150.

A synchronization operation of setting/maintaining desired clinical angles (LAO/RAO or CRA/CAU) by an operation about the main arm rotation axis Z2 and an operation about the arm slide axis Z3 while an operation about the column rotation axis Z1 is fixed (the rotation angle is fixed) is called a "clinical angle control operation".

In this clinical angle control operation, even if the holding apparatus main body 5 is inserted from any angle with respect to the object 150, it is possible to operate the C-arm 51 in the body axis direction/axis direction perpendicular to the body axis of the object 150 so as to implement the desired clinical angles (LAO/RAO or CRA/CAU).

An X-ray generation unit 1 is mounted on one end of the C-arm 51. An X-ray detector (generally called a flat panel detector (FPD)) 2 having a plurality of X-ray detection semiconductor elements arranged two-dimensionally is typically mounted on the other end of the C-arm 51.

The X-ray generation unit 1 includes an X-ray tube and an X-ray aperture mechanism for forming an X-ray irradiation field in an arbitrary shape such as a rectangle or circle. The X-ray aperture mechanism is supported to be rotatable about an imaging axis SA which connects the X-ray focus of the X-ray tube and the detection surface center of the X-ray detector 2. Similarly, the X-ray detector 2 is supported to be rotatable about the imaging axis SA.

Note that when the X-ray aperture mechanism forms a circular X-ray irradiation field, it is not always necessary to rotate the X-ray aperture mechanism about the imaging axis SA with the X-ray detector 2 in order to erect an image.

The imaging axis SA passing through the X-ray focus of the X-ray generation unit 1 and the detection surface center of the X-ray detector 2 is designed to intersect the main arm rotation axis Z2 and the arm slide axis Z3 at one point.

The absolute coordinates (the position on an imaging room coordinate system) of this intersection point do not displace unless the stand 53 rotates about the column rotation axis Z1 regardless of whether the C-arm 51 rotates about the main arm rotation axis Z2 or the arm slide axis Z3, as a matter of course. This intersection point is generally called an isocenter IS.

At the time of imaging, the object 150 is placed on a top 17 such that the body axis of the object 150 almost coincides with a baseline BL, as shown in FIG. 1. The baseline BL almost coincides with the center line of the top 17. The top 17 is provided on a bed 18 so as to be movable in a direction along a longitudinal direction parallel to the baseline BL and in a direction perpendicular to the longitudinal direction. The top 17 is provided on the bed 18 so as to be movable in a direction (vertical direction) perpendicular to the floor surface 59. That is, the bed 18 includes a top driving mechanism (operation axis) for driving the top 17 in the above-described directions.

The respective operation axes related to the above-described operations of the holding apparatus main body 5 and top 17 are configured to be individually operable electrically/manually. The X-ray diagnostic apparatus according to the embodiment includes a position sensor for generating data (to be referred to as position sensor data hereinafter) indicating the current position of each operation axis.

Interference points P serving as points of interest are set in portions (especially, portions with which interference (for example, contact) readily occurs) which reflect the outer shape of the X-ray diagnostic apparatus, as shown in FIG. 1. As more interference points P are set, more precise interference control becomes possible. However, it is preferable to set the number of interference points P in accordance with the throughput of a bed/holding apparatus controller 5C (to be described later).

Figure 2:
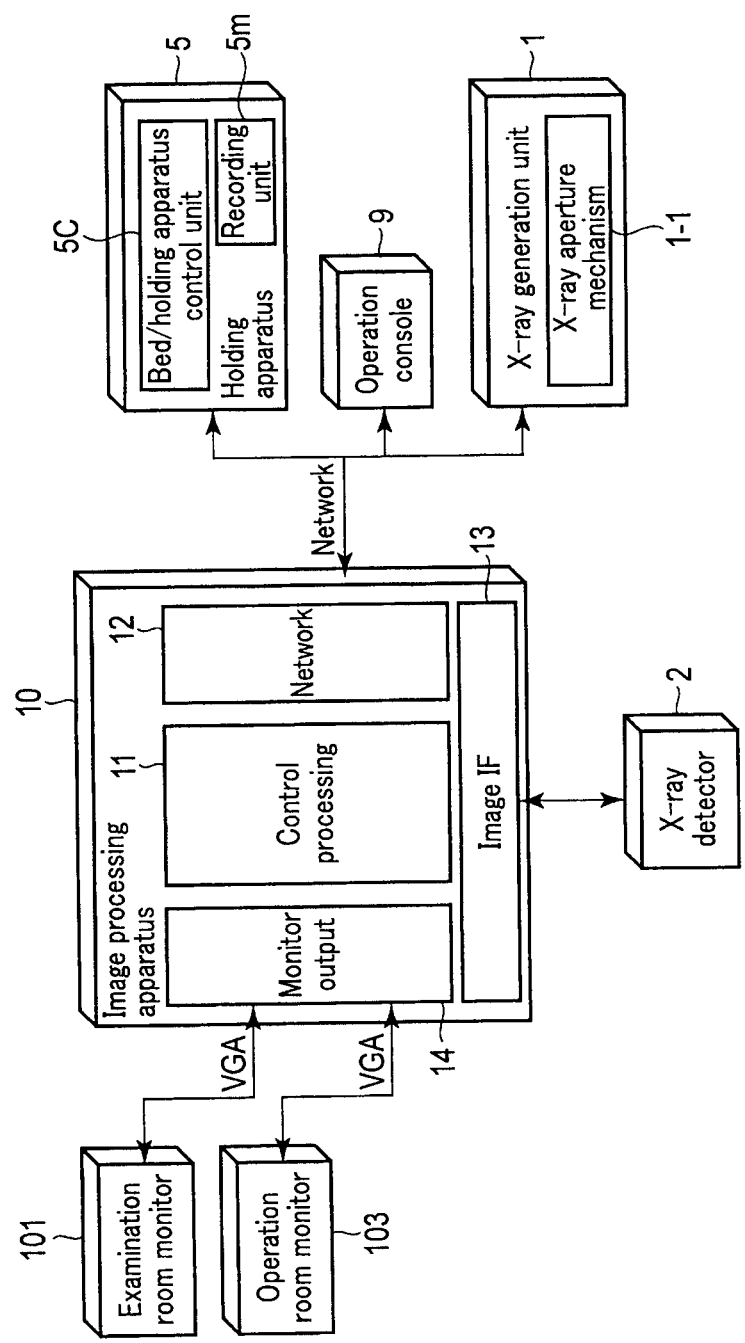
FIG. 2 is a block diagram showing an example of the system configuration of the X-ray diagnostic apparatus according to the embodiment.

FIG. 2 is a block diagram showing an example of the system configuration of the X-ray diagnostic apparatus according to the embodiment. The X-ray diagnostic apparatus according to this embodiment includes a processing apparatus 10 for performing image processing and the like. This processing apparatus 10 is communicably connected, via a network, to the bed/holding apparatus controller 5C for controlling driving of the X-ray generation unit 1, X-ray detector 2, and holding apparatus main body 5 and to an operation console 9 of the X-ray diagnostic apparatus.

The processing apparatus 10 includes a control processing unit 11, a network interface 12, an image interface 13, and a monitor output unit 14.

The control processing unit 11 includes processing circuitry and a memory, and comprehensively controls the image processing/display processing of medical image data collected by the X-ray diagnostic apparatus.

The network interface 12 is an interface for communicably connecting the X-ray generation unit 1, bed/holding apparatus controller 5C, and operation console 9.

The image interface 13 is an interface for inputting data collected by the X-ray detector 2.

The monitor output unit 14 is an interface for outputting predetermined medical image data to an examination room monitor 101 and an operation room monitor 103.

The X-ray generation unit 1 includes an X-ray tube (not shown) and an X-ray aperture mechanism 1-1. The X-ray tube is a vacuum tube which generates X-rays, and generates X-rays by accelerating electrons emitted from a cathode (filament) by a high voltage to bring them into contact with a tungsten anode. The X-ray aperture mechanism 1-1 is a means for limiting the X-ray irradiation range for irradiating only a desired imaging target portion with X-rays, and is provided to decrease the exposure dose of the object P and improve the image quality.

The X-ray detector 2 includes a flat panel detector (FPD), a gate driver, and a projection data generation unit. The FPD converts X-rays having passed through the region of interest of the object P into charges, and accumulates them. In this FPD, small detection elements for detecting X-rays are arranged two-dimensionally in the column and line directions. Each of the detection elements includes a photoelectric film for sensing X-rays and generating charges according to an incident X-ray dose, a charge accumulation capacitor for accumulating the charges generated by the photoelectric film, and a TFT (Thin-Film Transistor) for reading out, at a predetermined timing, the charges accumulated in the charge accumulation capacitor.

The operation console 9 generates an operation signal (operation request) in response to a user operation, and transmits the operation signal to the bed/holding apparatus controller 5C via the network. A program executed by the bed/holding apparatus controller 5C converts the operation signal (operation request) from the operation console 9 into a driving signal of each operation axis motor of the X-ray diagnostic apparatus, thereby executing/controlling operations from a simple individual mechanical angle axis operation to a complex multi-axis synchronization operation.

The examination room monitor 101 and operation room monitor 103 are monitors for displaying the medical image data output from the monitor output unit 14 of the processing apparatus 10.

The bed/holding apparatus controller 5C is a processor for executing interference control unique to the X-ray diagnostic apparatus according to this embodiment, in addition to normal clinical angle control, clinical angle correction control, and the like. That is, the bed/holding apparatus controller 5C drives the C-arm 51, arm holder 52, and stand 53 to execute clinical angle setting/maintenance control and interference control.

Since the respective operation axes of the above-described X-ray diagnostic apparatus can be individually operated electrically/manually, interference between the floor surface 59, wall surface (not shown), X-ray detector 2, X-ray generation unit 1, top 17, stand 53, and object 150 may occur within the movable ranges of the operation axes. Furthermore, interference may also occur between members other than those described above. To prevent such interference, the X-ray diagnostic apparatus according to this embodiment performs interference control as follows.

That is, the X-ray diagnostic apparatus according to this embodiment calculates the space coordinates (three-dimensional XYZ coordinates) of each interference point to hold them in time series (generates/holds a coordinate data group), and calculates vector data in consideration of the space coordinates calculated for a predetermined period until now (for example, for the several hundred ms until now), thereby performing interference control based on this vector data.

That is, the X-ray diagnostic apparatus according to this embodiment processes, as dynamic data (vector data) obtained in consideration of the moving speed and moving direction which have been calculated using the past space coordinates, data about each interference point which is processed as static data in the conventional technique, and performs efficient interference control based on the vector data.

Interference control by the X-ray diagnostic apparatus according to this embodiment will be described with reference to FIGS. 3, 4, and 5. In this embodiment, deceleration control, stop control, and warning control are prepared as interference control modes. An arbitrary combination of deceleration control, stop control, and warning control is applied to each of various interference targets, and the applicability of interference control is selected in accordance with whether interference targets are close to or away from each other and the moving directions, instead of simply applying interference control based on only the clearance between the interference targets.

Figure 3:
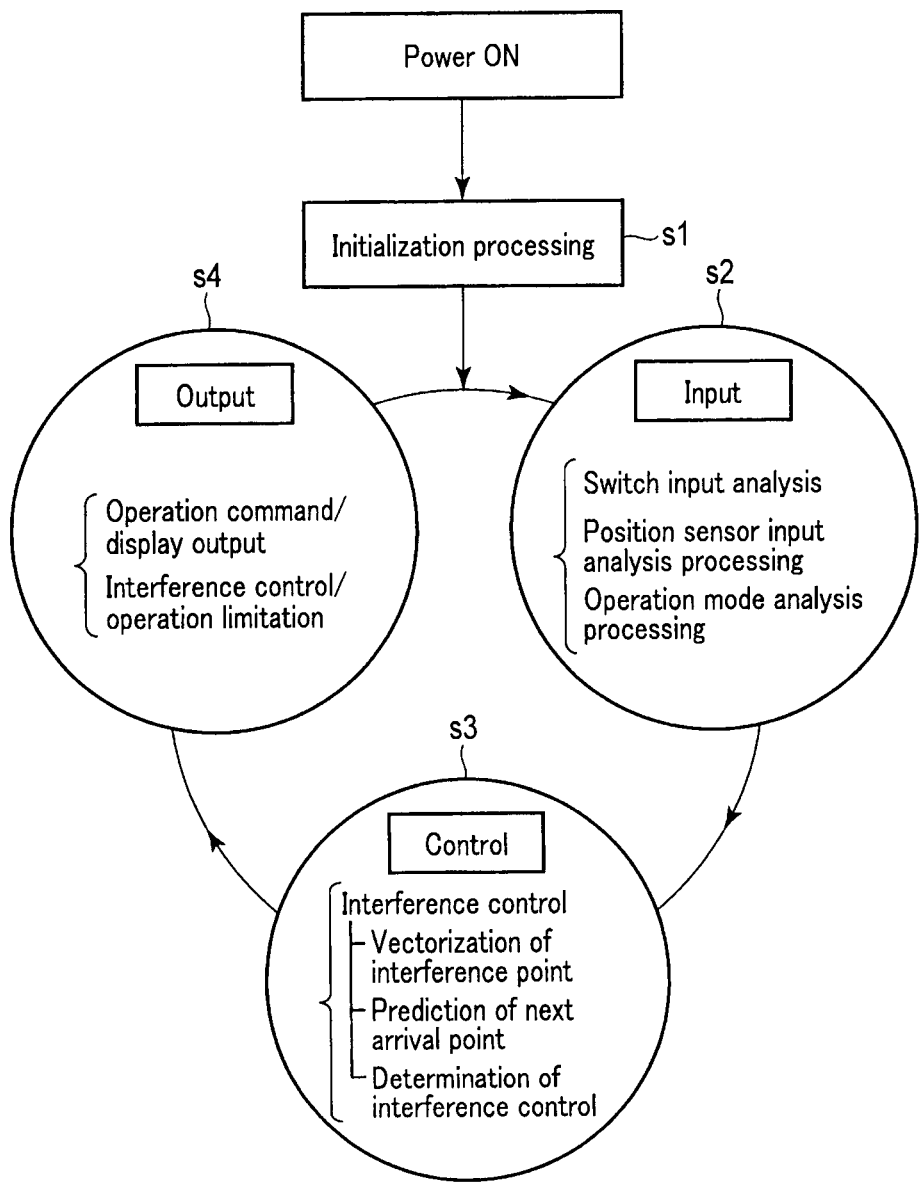
FIG. 3 is a view showing a processing sequence by a bed/holding apparatus controller.

FIG. 3 is a view showing a processing sequence (control loop) by the bed/holding apparatus controller 5C. Upon power-on of the X-ray diagnostic apparatus, the bed/holding apparatus controller 5C performs initialization processing (initialization step; step S1). That is, the bed/holding apparatus controller 5C initializes the network between the respective devices in the X-ray diagnostic apparatus shown in FIG. 5, and acquires information about each device via the network.

In this initialization step, the bed/holding apparatus controller 5C calculates the space coordinates (x, y, z) of the current position of each interference point at the time of initial setting, and then calculates the space coordinates in consideration of changes in the positions of the respective operation axes while performing the control loop (tracks the movement of each interference point). The space coordinates (x, y, z) indicate position data from the origin (0, 0, 0), which is formed by combining and reflecting the current positions of the respective operation axes. Note that the floor surface center of the bed 18 is set as the origin (0, 0, 0) of the space coordinate system. The bed/holding apparatus controller 5C functions as a coordinate calculation unit for calculating the space coordinates of each interference point.

The bed/holding apparatus controller 5C inputs the operation signal generated by the operation console 9 while loading predetermined firmware, and inputs the position sensor data indicating the current positions of the respective movable axes (input step; step S2). In step S2, based on the position sensor data generated by the position sensor provided for each of the above-described operation axes, the bed/holding apparatus controller 5C calculates the moving direction and moving speed of the operation axis. That is, step S2 is a step of executing so-called operation mode analysis, switch input analysis, and position sensor input analysis.

Figure 4:
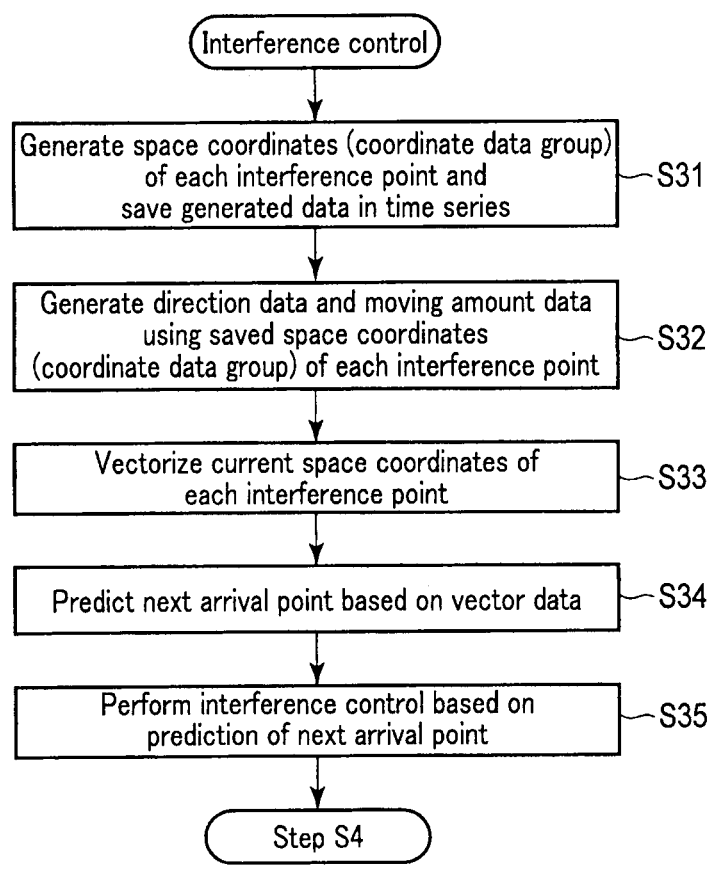
FIG. 4 is a flowchart illustrating processing for interference control by the bed/holding apparatus controller.

The bed/holding apparatus controller 5C sets a mode based on a processing result in step S2 to execute control of the mode, and performs interference control unique to the X-ray diagnostic apparatus according to the embodiment, which is described in a flowchart shown in FIG. 4 (control step; step S3). This interference control will be described below with reference to FIG. 4. FIG. 4 is a flowchart illustrating processing for interference control by the bed/holding apparatus controller 5C.

That is, the bed/holding apparatus controller 5C performs coordinate conversion of each interference point based on the position sensor data indicating the current positions of the respective operation axes acquired in step S2 and the like, generates the current space coordinates of each interference point, and records them in a recording unit 5m such as a memory (step S31). While repeatedly executing processing in the control loop, every time the processing in step S31 is performed, the space coordinates of each interference point are accumulated in time series in the recording unit 5m, thereby generating a coordinate data group for the interference point. That is, the recording unit 5m holds, in time series, the space coordinates of each interference point recorded at past points of time.

Subsequently, the bed/holding apparatus controller 5C generates direction data indicating the moving direction of each interference point and moving amount data indicating the moving amount of the interference point using the coordinate data group (the data indicating the space coordinates of the interference point at the past points of time saved in time series) recorded in the recording unit 5m (step S32).

Based on the direction data and moving amount data generated in step S32, the bed/holding apparatus controller 5C vectorizes the current space coordinates of each interference point (generates vector data) (step S33).

For example, based on the difference between the space coordinates (X, Y, Z) calculated in step S31 in the current control loop and those $(X^1, Y^1, Z^1)$ calculated in step S31 in the previous control loop, the bed/holding apparatus controller 5C calculates the moving direction and moving amount of the corresponding interference point.

If, for example, the processing results of the past n control loops can be used, it is possible to further improve the determination accuracy of interference control at the current interference point by using the space coordinates $(X^n, Y^n, Z^n)$. Note that as the value of n, an optimum value is set within an allowable range in consideration of the processing resource and processing speed of the bed/holding apparatus controller 5C.

Furthermore, the bed/holding apparatus controller 5C predicts the arrival coordinates of the interference point based on the vector data generated in step S33 (step S34). In other words, in step S34, based on the coordinate data group (past space coordinates), the bed/holding apparatus controller 5C calculates space coordinates (to be referred to as predicted arrival coordinates hereinafter) at which the interference point is estimated to be positioned at the time of next processing. The bed/holding apparatus controller 5C functions as an estimation unit for calculating the predicted arrival coordinates indicating space coordinates at which the interference point is estimated to arrive by movement based on the space coordinates recorded in time series in the recording unit 5m.

The bed/holding apparatus controller 5C determines processing contents of interference control based on the predicted arrival coordinates calculated in step S34 (step S35). After that, the process transits to step S4 shown in FIG. 3. Note that practical interference control processing/effects will be described in detail later.

After the processing in step S3 (steps S31 to S35 shown in FIG. 4), each device of the X-ray diagnostic apparatus is driven by a control signal such as an operation command/display output signal output from the bed/holding apparatus controller 5C (output step; step S4). That is, as interference control executed in step S4, interference control of the processing contents determined in step S35 is executed. That is, the bed/holding apparatus controller 5C functions as an interference controller for controlling each of the above-described operation axes (a mechanism for driving each unit of the top 17 and a mechanism for driving each unit of the holding apparatus main body 5) based on the predicted arrival coordinates.

Upon end of the processing in step S4, the process transits to step S2 again.

Interference control processing unique to the X-ray diagnostic apparatus according to this embodiment will be described in detail below. FIGS. 5, 6, 7, and 8 are views schematically showing interference control processing unique to the X-ray diagnostic apparatus according to this embodiment. Referring to FIGS. 5, 6, 7, and 8, reference numeral 200 denotes an interference target object for the interference points P. An arrow denoted by reference symbol V indicates the moving direction of the interference points P.

Figure 6:
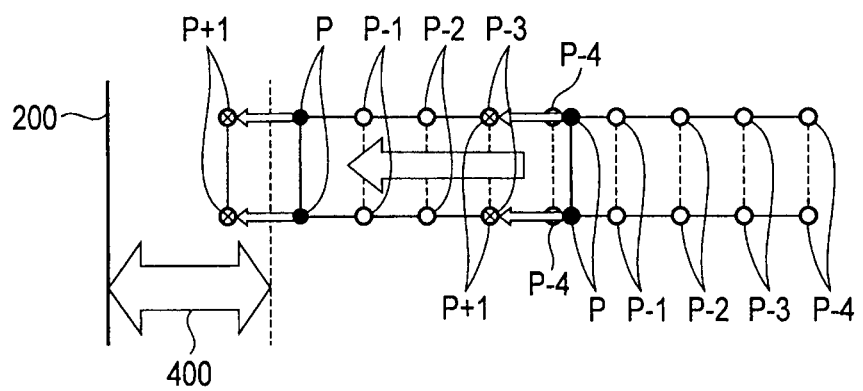
FIG. 6 is a view schematically showing the interference control processing of the X-ray diagnostic apparatus according to the embodiment of the present invention.
Figure 8:
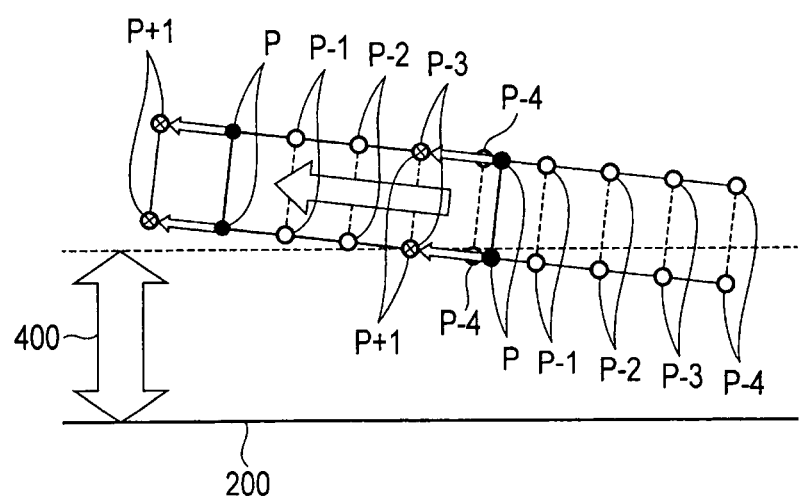
FIG. 8 is a view schematically showing the interference control processing of the X-ray diagnostic apparatus according to the embodiment of the present invention.

"Interference points P-n (n=1, 2, 3, 4) shown in FIGS. 6 and 8 indicate the positions of the interference points at the time of execution of the control loop n times before. In FIGS. 6 and 8, "interference points P+1" indicate the positions of the predicted arrival coordinates (in this example, coordinates at the time of execution of the next control loop).

A distance indicated by a double-headed arrow 400-S in FIGS. 5, 6, 7, and 8 is a threshold distance serving as a threshold when executing interference control. That is, when the distance between one interference point P+1 and the interference target object 200 becomes equal to or shorter than the threshold distance 400-S or 400-L, the bed/holding apparatus controller 5C controls to stop/decelerate the movement of the member (for example, the C-arm 51, arm holder 52, stand 53, top 17, or the like) provided with the interference point P. When the distance between one interference point P+1 and the interference target object 200 becomes equal to or shorter than the distance 400-L, the moving object is decelerated. When the distance between the interference point P+1 and the interference target object 200 becomes equal to or shorter than the distance 400-S shorter than the distance 400-L, the moving object is stopped. The distance 400-L will be referred to as a deceleration distance or deceleration region hereinafter. The distance 400-S will be referred to as a stop distance or stop region hereinafter.

Another example of interference control is, for example, processing of displaying a warning message on the display unit (not shown) of the operation console 9 or generating a warning sound by a loudspeaker unit (not shown) in addition to (or instead of) stopping/decelerating the movement as described above.

Note that the threshold distance 400-S is designed to be an appropriate value required for each interference point P and each interference target object 200, and recorded in advance in a memory (not shown) or the like.

Figure 5:
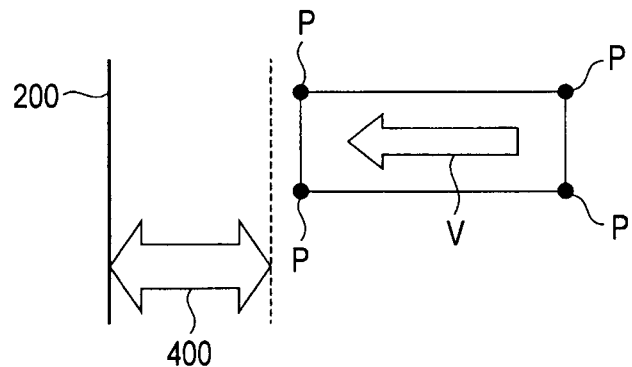
FIG. 5 is a view schematically showing the interference control processing of the X-ray diagnostic apparatus according to the embodiment of the present invention.

In the example shown in FIG. 5, each interference point P moves in a straight line toward the interference target object 200, and the distance between the interference target object 200 and the predicted arrival coordinates (the interference point P+1 shown in FIG. 6) becomes shorter than the threshold distance 400-S at the time of execution of the processing in the next control loop. In this case, the bed/holding apparatus controller 5C controls to stop/decelerate the movement of the interference point P. That is, the bed/holding apparatus controller 5C controls to stop/decelerate the movement of the member (for example, the C-arm 51, arm holder 52, stand 53, top 17, or the like) provided with the interference point P.

Note that in addition to (or instead of) stopping/decelerating the movement as described above, processing of displaying a warning message on the display unit (not shown) of the operation console 9 or generating a warning sound by the loudspeaker unit (not shown) may be performed, as a matter of course.

On the other hand, in conventional interference control, in the example shown in FIGS. 5 and 6, the space coordinates of each interference point are statically generated, and thus no interference control is performed before the distance between the interference point P and the interference target object 200 "actually" becomes shorter than the threshold distance 400-S. Therefore, in conventional interference control, it may be too late to perform interference control (too late to prevent contact or the like) when the moving speed of the interference point P is higher than expected, and the interference point P and the interference target object 200 are brought into contact with each other unless interference control of stopping/decelerating the movement immediately starts.

The X-ray diagnostic apparatus according to this embodiment calculates the position (predicted arrival coordinates) of the interference point P+1 at the time of execution of the processing in the next control loop using the coordinate data group obtained by holding the past space coordinates of the interference point in time series, and determines interference control based on the positional relationship between the predicted arrival coordinates and the interference target object 200. Therefore, it becomes possible to start interference control at an appropriate point of time (it is possible to prevent contact or the like caused by delay in the start time of interference control).

Figure 7:
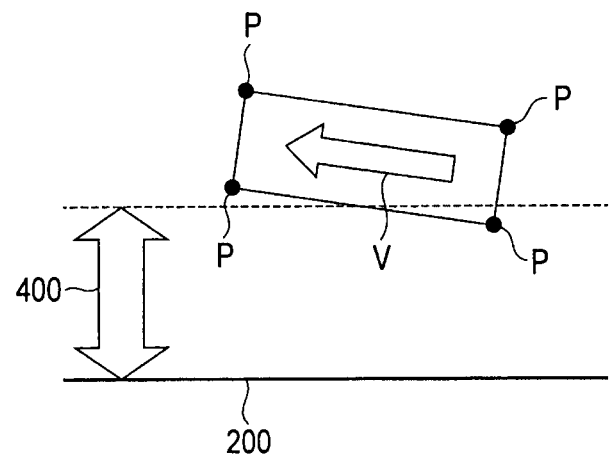
FIG. 7 is a view schematically showing the interference control processing of the X-ray diagnostic apparatus according to the embodiment of the present invention.

In the example shown in FIG. 7, although the distance between one interference point P and the interference target object 200 is shorter than the threshold distance 400-S, the interference point P moves in a direction away from the interference target object 200. It is expected that the distance between the predicted arrival coordinates (interference point P+1) and the interference target object 200 becomes equal to or longer than the threshold distance 400-S at the time of execution of the processing in the next control loop, as shown in FIG. 8.

In this case, the bed/holding apparatus controller 5C performs no interference control for the movement of the interference point P (does not control to stop/decelerate the movement of the interference point P). That is, the bed/holding apparatus controller 5C performs no interference control for the movement of the member (for example, the C-arm 51, arm holder 52, stand 53, top 17, or the like) provided with the interference point P (performs no member stop/deceleration processing or warning sound generation processing).

On the other hand, in conventional interference control, when the distance between at least one interference point and the interference target object 200 is shorter than the threshold distance 400-S as shown in the example of FIGS. 7 and 8, interference control is unwantedly performed. That is, although the interference point P and the interference target object 200 cannot be brought into contact with each other in consideration of the moving direction of the interference point, interference control is performed. Therefore, unnecessary stop/deceleration processing, processing of displaying a warning message on the display unit (not shown) of the operation console 9, and processing of generating a warning sound by the loudspeaker unit (not shown) are unwantedly performed.

The X-ray diagnostic apparatus according to this embodiment does not perform unnecessary interference control when there is no possibility that the interference point P and the interference target object 200 are actually brought into contact with each other even in a situation in which unnecessary interference control is unwantedly performed in conventional interference control. Therefore, for example, a passing operation or the like can be performed.

Note that in the above-described example, for the sake of descriptive convenience, the X-ray diagnostic apparatus for performing a three-axis rotation operation is assumed but this embodiment is also applicable to an X-ray diagnostic apparatus having an operation mode using four or more rotation axes. The embodiment is applicable to not only the X-ray diagnostic apparatus according to the above-described aspect but also a ceiling suspended type X-ray diagnostic apparatus, an X-ray diagnostic apparatus called an RF apparatus, and the like. This embodiment is also applicable to an X-ray diagnostic apparatus for performing interference control using a contact sensor/non-contact sensor.

More detailed interference control will be explained below.

FIG. 9 shows interference control for the patient placed on the top 17. A semicylindrical region having the center line of the top 17 as a center and a radius of 300 mm from the upper surface of the top 17 is set as an interference area, and interference control is performed by setting the region as a deceleration region 21. When the interference point P of the X-ray detector 2 or the like comes closer to the deceleration region 21, and reaches the deceleration region 21, the approach speed such as the rotation of the c-arm 51 or the forward/backward movement of the X-ray detector 2 is decelerated. The reason why the movement is not stopped but decelerated is that the operator can visually confirm the interference point P of the X-ray detector 2 or the like moving closer to the object and thus adequately avoid contact by decelerating the movement, and that the situation in which fine adjustment of the imaging angle is limited is suppressed. Note that deceleration control functions only when the interference point P of the X-ray detector 2 or the like comes closer to the deceleration region 21, and does not function when the interference point P of the X-ray detector 2 or the like moves away from the top 17 or parallel to the front surface of the top 17. This can move or retract the X-ray detector 2 or the like to a target position within a short time.

FIG. 10 shows interference control with respect to the bottom surface of the top 17. A region of, for example, 150 mm from the bottom surface of the top 17 is set as an interference area, and interference control is performed by setting the region as a deceleration region 22. When the interference point P of the X-ray generation unit 1 or the like comes closer to the deceleration region 22 and reaches the deceleration region 22, the approach speed such as the rotation of the C-arm 51 or the forward/backward movement of the X-ray generation unit 1 is decelerated. Since the bottom surface of the top 17 is a blind spot for the operator, a region closer to the bottom surface of the top 17 than the deceleration region 22, for example, a region of 100 mm from the bottom surface of the top 17 is set as an interference area, and interference control is performed by setting the region as a warning region 23. When the interference point P of the X-ray generation unit 1 or the like comes closer to the warning region 23 and reaches the warning region 23, a warning sound is generated. Even if the interference point P of the X-ray generation unit 1 or the like is positioned within the warning region 23, when it moves in a direction away from the top 17 or stays still, no warning sound is generated. By providing the deceleration region 22 and warning region 23 without providing any stop region, it is possible to suppress the situation in which fine adjustment of the imaging angle is limited. Note that the thickness of the top 17 may be considered as a constant value but it is preferable to set a region of, for example, 250 mm from the bottom surface of the top 17 as the deceleration region 22 on the foot side of the top in consideration of the thickness.

FIG. 11 shows interference control around the side surface of the top 17. A region of, for example, 200 mm from the side end of the top 17 is set as an interference area. When the region is set as a deceleration region 24, and the interference point P of the X-ray generation unit 1 or the like comes closer to the side surface of the top 17, and reaches the deceleration region 24, the approach operation by the rotation of the C-arm 51 or the forward/backward movement of the X-ray generation unit 1 is decelerated. Since the width of the top 17 is not constant, the deceleration region 24 is formed in a shape in consideration of the width. Since the side surface of the top 17 is a blind spot for the operator, similarly to the bottom surface, a region closer to the side surface of the top 17 than the deceleration region 24, for example, a region of 100 mm from the side surface of the top 17 is set as an interference area, and the region is set as a warning region 25, thereby performing interference control. When the interference point P of the X-ray generation unit 1 or the like comes closer to the warning region 25, and reaches the warning region 25, a warning sound is generated. Even if the interference point P of the X-ray generation unit 1 or the like falls within the warning region 25, when it moves in a direction away from the side surface of the top 17 or stays still, no warning sound is generated. Note that the clearance between the interference point and the side surface of the top 17 at a set position is small depending on a model, a small warning sound may be generated all the time, and thus no warning region is provided and only a deceleration operation may be performed without generating a warning sound.

Figure 12:
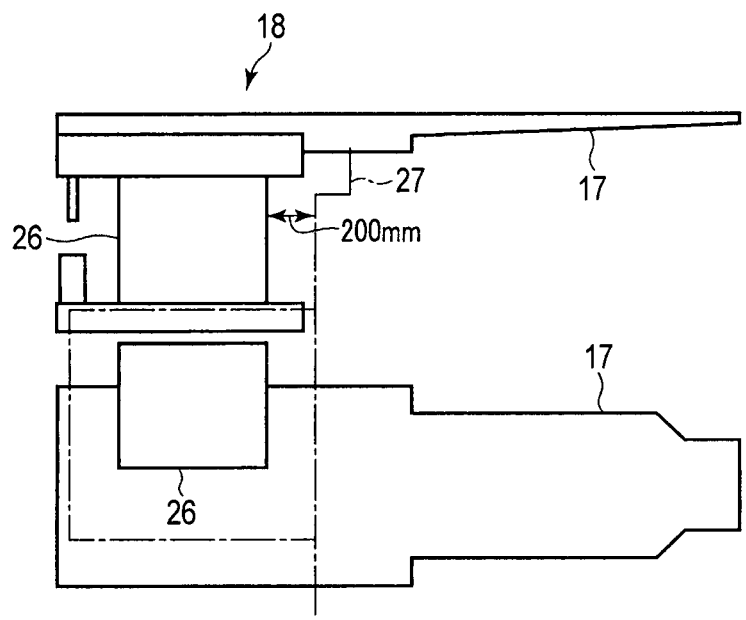
FIG. 12 is a view showing a deceleration region and stop region with respect to the bed column portion of the X-ray diagnostic apparatus according to the embodiment of the present invention.

As shown in FIG. 12, a region of, for example, 200 mm around a column portion 26 of the bed 18 is set as an interference area. When the region is set as a deceleration region 27, and the interference point P of the X-ray generation unit 1 or the like comes closer to the column portion 26 of the bed 18 and reaches the deceleration region 27, the approach operation to the column portion 26 of the bed 18 by the rotation of the C-arm 51 or the like is decelerated. Furthermore, a region of, for example, 80 mm around the column portion 26 of the bed 18 is set as a stop region, and the approach operation to the column portion 26 of the bed 18 by the rotation of the C-arm 51 or the like is stopped.

Figure 13:
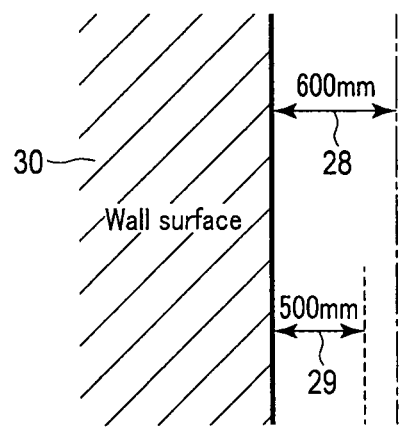
FIG. 13 is a view showing a deceleration region and stop region with respect to a wall surface according to the embodiment of the present invention.

As shown in FIG. 13, a region of, for example, 600 mm from a wall surface 30 of an imaging room is set as a deceleration region 28, and a region of, for example, 500 mm from the wall surface 30 of the imaging room is set as a stop region 29. When the interference point P of the X-ray generation unit 1 or the like comes closer to the wall surface 30 of the imaging room and reaches the deceleration region 28, the approach operation of the interference point P to the wall surface 30 of the imaging room by the rotation of the C-arm 51 or the like is decelerated. Furthermore, when the interference point P comes closer to the wall surface 30 of the imaging room, and reaches the stop region 29, the operation is stopped. By providing the stop region 29 in addition to the deceleration region 28, setting a region of 600 mm as the deceleration region 28, and setting a region of 500 mm as the stop region 29, it is possible to avoid a situation in which the operator or the like is sandwiched between the wall surface 30 and the C-arm 51 or the like.

Figure 14:
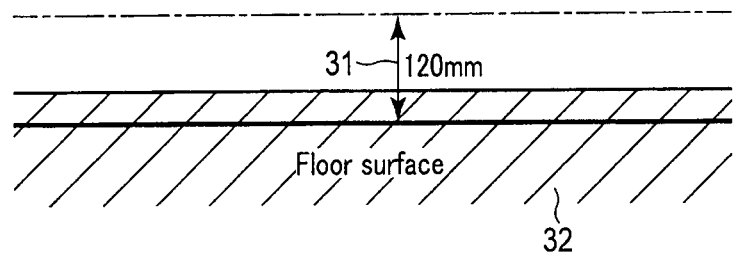
FIG. 14 is a view showing a deceleration region and stop region with respect to a floor surface according to the embodiment of the present invention.

As shown in FIG. 14, a region of, for example, 120 mm from a floor surface 32 is set as a temporary stop region 31. When the interference point P of the X-ray generation unit 1 or the like comes closer to the floor surface 32 and reaches the temporary stop region 31 by sliding of the C-arm 51 or the like, the approach operation of the interference point P of the X-ray generation unit 1 or the like to the floor surface 32 is temporarily stopped. After temporary stop, the approach operation of the interference point P to the floor surface 32 by sliding of the C-arm 51 or the like is permitted when the operator or the like performs a re-operation. At the time of the re-operation, a warning sound is continuously generated during the operation to call attention to the operator. The distance of the temporary stop region 31 is defined for each model in accordance with the vertical position of the X-ray detector 2/X-ray generation unit 1 with respect to the C-arm 51. It is possible to avoid the foot of the operator or the like from getting caught by approaching the floor surface 32, and relax a movement limitation.

In a biplane system including two imaging systems, interference between the C-arm of one imaging system (floor type) and the Ω-arm of the other imaging system (ceiling suspended type), interference between the X-ray detector of the one imaging system and that of the other imaging system, interference between the X-ray detector/X-ray tube cover/column rear portion of the one imaging system and the X-ray detector/X-ray tube cover of the other imaging system, interference between the inside portion of the C-arm of the one imaging system and the X-ray detector/X-ray tube cover of the other imaging system, and interference between the floor base portion of the one imaging system and the other imaging system are also controlled to avoid them, as follows.

Figure 15A:
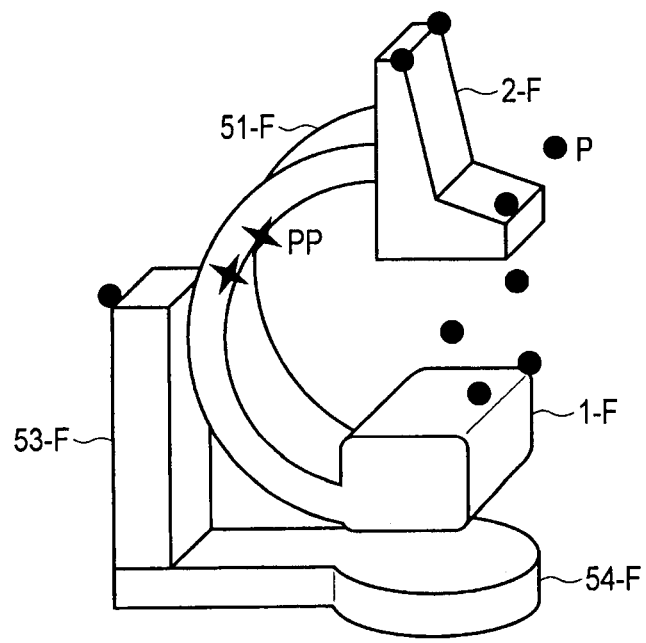
FIG. 15A is the first supplementary view showing interference control for the overall arm of the X-ray diagnostic apparatus according to the embodiment of the present invention.
Figure 15B:
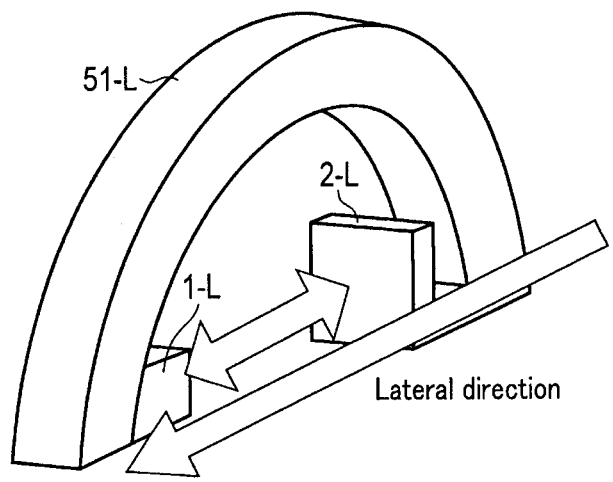
FIG. 15B is the second supplementary view showing interference control for the overall arm of the X-ray diagnostic apparatus according to the embodiment of the present invention.

As shown in FIGS. 15A and 15B, with respect to interference between a C-arm 51-F of one imaging system and an Ω-arm 51-L of the other imaging system, under the conditions of the ceiling longitudinal/lateral movement of the Ω-arm 51-L of 0 cm, the vertical movement of the detector/tube of 0 cm, a clearance defined by the SID between the imaging systems, a CAD derives the moving range when the arm rotation/arm slide operations of the arms 51-F and 51-L are performed. The control processing is performed based on the interference table, and the operation of the rotating arm 51-F or 51-L is stopped when the clearance of the arm 51-L with respect to the interference point P of the arm 51-F is equal to or smaller than 40 mm. With respect to the arm operation, a deceleration operation in two stages, that is, two deceleration regions having clearances of 50 mm or smaller and 60 mm or smaller are adopted, thereby ensuring safety. The interference table is created for the size of each of X-ray detectors 2-F and 2-L and the size of an aperture depending on the type of aperture formed in each imaging system. In the interference table, deceleration regions should be arbitrarily optimized according to the moving directions of the imaging systems. A warning sound is generated while performing deceleration control. After stopping the movement, when a moving operation is performed again, movement at a low speed after deceleration is permitted. This interference control operation is effective only within the allowable range of the isocenter, and a region outside the range is always considered as an interference region to call attention by a low-speed operation and warning sound.

With respect to interference between the X-ray detector 2-F of the one imaging system and the X-ray detector 2-L of the other imaging system, a deceleration region and stop region (clearance) are calculated, and the operation is stopped and decelerated according to the clearance. Note that only the deceleration region can be provided, without providing a stop region, for movement in the ceiling longitudinal and lateral directions of the X-ray detector 2-F of the one imaging system. A warning sound is generated while performing deceleration control. After stopping the movement, when a moving operation is performed again, movement at a low speed after deceleration is permitted. This interference control operation is effective only within the allowable range of the isocenter, and a region outside the range is always considered as an interference region to call attention by a low-speed operation and warning sound.

With respect to interference control of the X-ray detector 2-L and the tube cover of an X-ray generation unit 1-L of the other imaging system with the X-ray detector 2-F, the tube cover of an X-ray generation unit 1-F, and a column rear portion 53-F of the one imaging system, when the other imaging system falls outside the isocenter range of the one imaging system, it is determined whether the interference points P of the X-ray detector 2-F, the tube cover of the X-ray generation unit 1-F, and the column rear portion 53-F fall within a range from the front surface of the detector 2-L to the front surface of the tube cover of the X-ray generation unit 1-L. If the interference points P fall within the range, the other imaging system (ceiling suspended type) can pass through the one imaging system (floor type), and thus the ceiling longitudinal operation is possible. If the interference point falls outside the range, the clearance between the interference point P and the X-ray detector 2-L or the tube cover of the X-ray generation unit 1-L of the other imaging system is calculated. When the clearance is equal to or smaller than 200 mm, the operation is stopped.

With respect to interference control of the X-ray detector 2-L and the tube cover of the X-ray generation unit 1-L of the other imaging system with an arm inside portion PP of the one imaging system, when the X-ray detector 2-L and X-ray generation unit 1-L of the other imaging system fall outside the isocenter range of the one imaging system, as exemplified in FIGS. 15A and 15B, it is determined whether the interference point PP of the arm inside portion of the one imaging system falls within a range from the front surface of the detector 2-L to the front surface of the tube cover of the X-ray generation unit 1-L. If the interference point PP falls within the range, the other imaging system (ceiling suspended type) can pass through the one imaging system (floor type), and thus the ceiling longitudinal operation is possible. If the interference point falls outside the range, the clearance between the interference point and the X-ray detector 2-L or the tube cover of X-ray generation unit 1-L of the other imaging system is calculated. When the clearance is equal to or smaller than 200 mm, the operation is stopped. Note that in a lower extremity mode, the one imaging system (floor type) is positioned very close to the other imaging system (ceiling suspended type) by utilizing the floor rotation/column rotation of the one imaging system. Therefore, it is inevitable that the clearance becomes 200 mm or less, and when the X-ray detector 2-L or the tube cover of the X-ray generation unit 1-L of the other imaging system interferes with the arm inside portion of the normal one imaging system, the one imaging system cannot reach a target position in the lower extremity mode. To solve this problem, in an automatic positioning operation in the lower extremity mode set as a target position in advance, interference control of the X-ray detector 2-L and the tube cover of the X-ray generation unit 1-L of the other imaging system with respect to the arm inside portion of the one imaging system is canceled.

Figure 16:
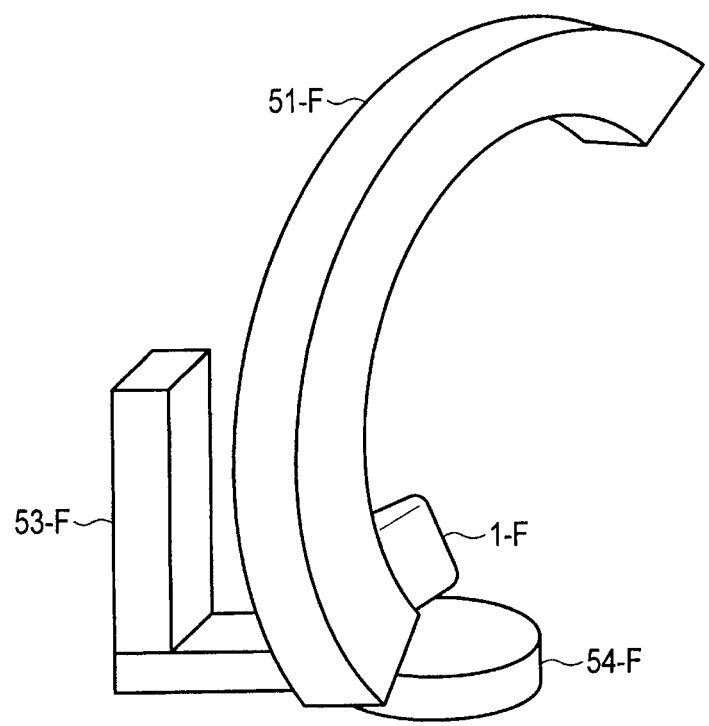
FIG. 16 is a supplementary view showing interference control for the floor base of the X-ray diagnostic apparatus according to the embodiment of the present invention.

As shown in FIG. 16, the other imaging system comes closer to a floor base portion 54-F of the one imaging system (floor type) by an arm slide operation and, at a park position, a horizontal operation (arm rotation/ceiling longitudinal operation). Therefore, the clearance with the floor base portion 54-F is calculated, and the approach operation to the floor base portion 54-F is decelerated when the clearance is 200 mm or less. When the clearance is 100 mm or less, the approach operation is stopped.

To switch between LL (lateral/lateral imaging) and RL (frontal/lateral imaging), when the other imaging system (ceiling suspended type) comes closer to the one imaging system (floor type) which has been retracted, operation control is performed to decelerate the rotations of the arms 51L and 51F and not to stop the operation.

In this embodiment, the presence/absence of deceleration control, warning sound generation control, and stop control for the interference control target will be described below. For the patient barrier (FIG. 9), only deceleration control is performed and no warning sound generation control or stop control is performed. For the bottom surface of the bed/top (FIG. 10), deceleration control and warning sound generation control are performed but no stop control is performed. For the bed column portion (FIG. 12), deceleration control and stop control are performed but no warning sound generation control is performed. For a region around the bed/top and a front end portion thereof (FIG. 11), deceleration control and warning sound generation control are performed but no stop control is performed. With respect to a wall surface on the right side of the patient, a wall surface on the left side of the patient, a wall surface on the head side of the patient (FIG. 13), the floor surface (FIG. 14), the overall arms (FIGS. 15A and 15B), a CT main body, and a CT base, deceleration control and stop control are performed but no warning sound generation control is performed. For a BP-CAS main body and BP-CAS detector, all of deceleration control, waning sound generation control, and stop control are performed.

As described above, according to this embodiment, it is possible to provide an X-ray diagnostic apparatus for performing interference control and a control method for the X-ray diagnostic apparatus and, more particularly, an X-ray diagnostic apparatus for implementing appropriate interference control in consideration of the operating direction and operating speed of each operation axis, and a control method for the X-ray diagnostic apparatus.

That is, with the X-ray diagnostic apparatus and the control method for the X-ray diagnostic apparatus according to this embodiment, it is possible to detect a future change in the relative positional relationship between an interference point and an interference target object (for example, a situation in which the distance between them becomes shorter, a situation in which the distance becomes longer, or a situation in which they are to pass each other), and thus it is possible to perform appropriate interference control such as stop/deceleration processing, processing of displaying a warning message on the display unit (not shown) of the operation console 9, and processing of generating a warning sound by the loudspeaker unit (not shown) at appropriate timings. Therefore, a more efficient operation can be advanced, as compared with a case in which the X-ray diagnostic apparatus for performing conventional interference control is used, thereby improving the efficiency of the operation progress and the operability.

In other words, the X-ray diagnostic apparatus and the control method for the X-ray diagnostic apparatus according to this embodiment implement interference control at a timing in consideration of the operating speed of a member provided with an interference point, and suppress an interference control operation when a passing operation considering the operating direction is predicted. Therefore, the operability of the system of the X-ray diagnostic apparatus is improved, and improved interference control can efficiently advance the operation.

More specifically, with the X-ray diagnostic apparatus and the control method for the X-ray diagnostic apparatus according to this embodiment, even if an operation is performed so that the interference point comes closer to the interference target object, it is possible to continue the operation to a minimum distance while ensuring safety without starting interference control by slowly moving the operating axis related to the operation. Note that if the speed at which the interference point and the interference target object come closer to each other is a predetermined speed or higher, interference control (stop/deceleration processing) is performed at a timing with sufficient time to prevent the interference point and the interference target object from being brought into contact with each other.

On the other hand, in conventional interference control, space coordinates reflecting the position of each operation axis are calculated, the distance between each interference point and the interference target is calculated every time (for each point of time), and interference control is performed based on only the calculation result. That is, in conventional interference control, the operating speed and operating direction of each interference point are not reflected in interference control, and only the distance (interval) between the interference point and the interference target object at each point of time is used to determine the possibility that they come into contact with each other.

In conventional interference control, since the operating speed is not taken into consideration as described above, when the speed at which the interference point comes closer to the interference target object is low, the deceleration section is unnecessarily large (because unnecessary stop/deceleration processing is performed) and thus the operation efficiency degrades, and when the speed is high, the deceleration section may be insufficient and thus interference control may be performed too late (the interference point and the interference target object may come into contact with each other).

Furthermore, in conventional interference control, since the operating direction is not taken into consideration as described above, it is difficult to determine whether the interference point moves closer to or away from the interference target object. Even in an operation in which the interference point simply passes the interference target object without contacting it, interference control may be unwantedly performed to execute stop/deceleration processing.

The above-described problems with conventional interference control are solved by the X-ray diagnostic apparatus and the control method for the X-ray diagnostic apparatus according to this embodiment.

The above described "processing circuitry" means, for example, a central processing unit (CPU), a graphics processing unit (GPU), an application specific integrated circuit (ASIC), a programmable logical device (e.g., a simple programmable logic device (SPLD), a complex programmable logic device (CPLD), and a field programmable gate array (FPGA)), or the like.

Note that programs may be directly incorporated in processing circuitry instead that programs are stored in a memory 5m. In this case, the processing circuitry reads programs incorporated in circuitry and executes the programs to realize predetermined functions.

Each function (each component) in the present embodiment is not necessary to be corresponded to a single processing circuit and may be realized by a plurality of processing circuits. To the contrary, for example, at least two functions (at least two components) may be realized by a single processing circuit. Further, a plurality of functions (a plurality of components) may be realized by a single processing circuit.

Although some embodiments of the present invention have been explained, these embodiments are presented as examples, and do not intend to limit the scope of the invention. These novel embodiments can be practiced in various other aspects, and various omissions, replacements, and changes can be made without departing from the spirit of the invention. These embodiments and their modifications are included in the scope and spirit of the invention, and are also included in inventions described in the scope of the claims and their equivalent scope.

The invention claimed is:
1. An X-ray diagnostic apparatus, comprising:
a top;
a bed configured to movably hold the top;
an X-ray tube configured to irradiate an object placed on the top with X-rays;
an X-ray detector arranged to face the X-ray tube and configured to generate X-ray projection data by detecting the X-rays emitted by the X-ray tube;
a supporting arm configured to movably support the X-ray tube and the X-ray detector;
a holder configured to movably hold the supporting arm; and
control processing circuitry configured to control a support unit that includes at least one of the bed, the supporting arm, and the holder to move a move unit that includes at least one of the top, the X-ray tube, the X-ray detector, and the supporting arm
wherein the control processing circuitry is further configured to
calculate arrival space coordinates, which are space coordinates predicted to be reached by movement of a mobile body based on vector data representing a movement amount and a movement direction in space coordinates of the mobile body, the mobile body being a region of interest set on a surface of the move unit, and control the support unit in accordance with a distance between the calculated arrival space coordinates of the region of interest and space coordinates of an interference object.

2. The X-ray diagnostic apparatus of claim 1, wherein the control processing circuitry is further configured to apply deceleration control to movement of the supporting arm when one of the X-ray tube and the X-ray detector comes closer to a front surface of the top within a predetermined distance, and not to apply the deceleration control when the one of the X-ray tube and the X-ray detector moves away from the front surface of the top or moves almost parallel to the front surface of the top.

3. The X-ray diagnostic apparatus of claim 1, wherein the control processing circuitry is further configured to apply, to movement of the supporting arm, one of deceleration control and warning control for generating a warning sound when one of the X-ray tube and the X-ray detector comes closer to a bottom surface of the top, and apply neither the deceleration control nor the warning control when the one of the X-ray tube and the X-ray detector moves away from a front surface of the top.

4. The X-ray diagnostic apparatus of claim 1, wherein the control processing circuitry is further configured to apply, to movement of one of the top and the supporting arm, deceleration control and warning control for generating a warning sound when one of the X-ray tube, the X-ray detector, and the holder comes closer to a side of the top, and apply neither the deceleration control nor the warning control when the one of the X-ray tube and the X-ray detector moves in one of a direction away from the side of the top and a direction parallel to the side of the top.

5. The X-ray diagnostic apparatus of claim 1, wherein the control processing circuitry is further configured to apply one of deceleration control and stop control to movement of the supporting arm when one of the X-ray tube, the X-ray detector, and the holder comes closer to a bed column portion, and apply neither the deceleration control nor the stop control when the one of the X-ray tube, the X-ray detector, and the holder moves away from the bed column portion.

6. The X-ray diagnostic apparatus of claim 1, wherein the control processing circuitry is further configured to apply one of deceleration control and stop control to movement of the supporting arm when one of the X-ray tube, the X-ray detector, and the holder comes closer to a wall surface, and apply neither the deceleration control nor the stop control when the one of the X-ray tube, the X-ray detector, and the holder moves away from the bed.

7. The X-ray diagnostic apparatus of claim 1, wherein the control processing circuitry is further configured to apply temporary stop control to movement of the supporting arm when one of the X-ray tube, the X-ray detector, and the holder comes closer to a floor surface, and apply movement control while generating a warning after a temporary stop.

8. The X-ray diagnostic apparatus of claim 1, further comprising:
another bed configured to movably hold another top;
another X-ray tube;
another X-ray detector arranged to face the other X-ray tube and configured to generate other X-ray projection data by detecting X-rays emitted by the other X-ray tube;
another supporting arm configured to movably hold the other X-ray tube and the other X-ray detector; and
another holder configured to movably support the supporting arm,
wherein the control processing circuitry is further configured to apply one of deceleration control and stop control to movement of one of the supporting arm and the other supporting arm when the supporting arm and the other supporting arm come closer to each other, and apply neither the deceleration control nor the stop control when the supporting arm and the other supporting arm move away from each other.

9. The X-ray diagnostic apparatus of claim 1, further comprising:
another top;
another bed configured to movably hold the another top;
another X-ray tube;
another X-ray detector arranged to face the other X-ray tube and configured to generate other X-ray projection data by detecting X-rays emitted by the other X-ray tube;
another supporting arm configured to movably hold the other X-ray tube and the other X-ray detector; and
another holder configured to movably support the supporting arm,
wherein the control processing circuitry is further configured to apply one of deceleration control and stop control when the X-ray detector and the other X-ray detector come closer to each other, and apply neither the deceleration control nor the stop control when the X-ray detector and the other X-ray detector move away from each other.

10. An X-ray diagnostic apparatus, comprising:
a bed column portion configured to movably hold a top;
an X-ray tube configured to irradiate an object placed on the top with X-rays;
an X-ray detector arranged to face the X-ray tube and configured to generate X-ray projection data by detecting the X-rays emitted by the X-ray tube;
a supporting arm configured to movably hold the X-ray tube and the X-ray detector;
a holder configured to movably support the supporting arm; and
a control processing circuitry configured to control a support unit that includes at least one of the bed, the supporting arm, and the holder to move a move unit that includes at least one of the top, the bed column portion, the X-ray tube, the X-ray detector, the supporting arm, and a wall surface and floor surface of an examination room,
wherein the control processing circuitry is further configured to
calculate arrival space coordinates, which are space coordinates predicted to be reached by movement of a mobile body based on vector data representing a movement amount and a movement direction in space coordinates of the mobile body, the mobile body being a region of interest set on a surface of the move unit, and
control the support unit in accordance with a distance between the calculated arrival space coordinates of the region of interest and space coordinates of an interference object.

11. The X-ray diagnostic apparatus of claim 10, wherein the control processing circuitry is further configured to apply deceleration control for decelerating movement of the supporting arm when one of the X-ray tube and the X-ray detector comes closer to a front surface of the top.

12. The X-ray diagnostic apparatus of claim 10, wherein the control processing circuitry is further configured to apply deceleration control for decelerating movement of the supporting arm and warning control for generating a warning sound when one of the X-ray tube and the X-ray detector comes closer to a bottom surface of the top.

13. The X-ray diagnostic apparatus of claim 10, wherein the control processing circuitry is further configured to apply deceleration control for decelerating movement of one of the top and the supporting arm and warning control for generating a warning sound when one of the X-ray tube, the X-ray detector, and the holder comes closer to a side of the top.

14. The X-ray diagnostic apparatus of claim 10, wherein the control processing circuitry is further configured to apply deceleration control for decelerating movement of the supporting arm and stop control when one of the X-ray tube, the X-ray detector, and the holder comes closer to the bed column portion.

15. The X-ray diagnostic apparatus of claim 10, wherein the control processing circuitry is further configured to apply deceleration control for decelerating movement of the supporting arm and stop control when one of the X-ray tube, the X-ray detector, and the holder comes closer to the wall surface.

16. The X-ray diagnostic apparatus of claim 10, wherein the control processing circuitry is further configured to apply control for temporarily stopping movement of the supporting arm when one of the X-ray tube, the X-ray detector, and the holder comes closer to the floor surface, and apply movement control while generating a warning after the temporary stop.

17. The X-ray diagnostic apparatus of claim 10, further comprising:
   another bed column portion configured to movably hold another top;
   another X-ray tube;
   another X-ray detector arranged to face the other X-ray tube and configured to generate other X-ray projection data by detecting X-rays emitted by the other X-ray tube;
   another supporting arm configured to movably hold the other X-ray tube and the other X-ray detector; and
   another holder configured to movably support the supporting arm,
   wherein the control processing circuitry is further configured to apply deceleration control for decelerating movement of one of the supporting arm and the other supporting arm and stop control when the supporting arm and the other supporting arm come closer to each other.

18. The X-ray diagnostic apparatus of claim 10, further comprising:
   another bed column portion configured to movably hold another top;
   another X-ray tube;
   another X-ray detector arranged to face the other X-ray tube and configured to generate other X-ray projection data by detecting X-rays emitted by the other X-ray tube;
   another supporting arm configured to movably hold the other X-ray tube and the other X-ray detector; and
   another holder configured to movably support the supporting arm,
   wherein the control processing circuitry is further configured to apply one of deceleration control and stop control when the X-ray detector and the other X-ray detector come closer to each other.

19. An X-ray diagnostic apparatus, comprising:
   a top;
   a bed configured to movably hold the top;
   an X-ray tube configured to irradiate an object placed on the top with X-rays;
   an X-ray detector arranged to face the X-ray tube and configured to generate X-ray projection data by detecting the X-rays emitted by the X-ray tube;
   a supporting arm configured to movably support the X-ray tube and the X-ray detector;
   a holder configured to movably hold the supporting arm; and
   control processing circuitry configured to
      define a plurality of interference points, including at least one interference point on at least two of the top, the bed, the X-ray tube, the X-ray detector, the supporting arm, and the holder,
      store space coordinates of each interference point of the plurality of interference points at a plurality of times,
      determine a velocity vector, representing a movement direction and a movement speed, for each of the plurality of interference points, based on the stored space coordinates,
      predict arrival space coordinates at a next time for each of the plurality of interference points, based on the determined velocity vector of each of the plurality of interference points,
      determine a distance between a pair of the plurality of interference points, based on the predicted arrival space coordinates of the pair of interference points, and
      perform interference control based on the determined distance.

* * * * *